United States Patent
de Paulis et al.

(10) Patent No.: US 6,693,128 B2
(45) Date of Patent: Feb. 17, 2004

(54) SUBSTITUTED DICINNAMOYLQUINIDES AND THEIR USE IN AUGMENTATION OF ADENONSINE FUNCTION

(75) Inventors: Tomas de Paulis, Hermitage, TN (US); David M. Lovinger, Rockville, MD (US); Peter Martin, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 10/143,606

(22) Filed: May 10, 2002

(65) Prior Publication Data

US 2003/0013758 A1 Jan. 16, 2003

Related U.S. Application Data

(60) Provisional application No. 60/290,282, filed on May 11, 2001.

(30) Foreign Application Priority Data

May 16, 2001 (CA) .............................. 2347879

(51) Int. Cl.$^7$ ................................ A61K 31/34
(52) U.S. Cl. .................................... 514/473
(58) Field of Search ......................... 514/473

(56) References Cited

U.S. PATENT DOCUMENTS

| 5,262,167 A | * 11/1993 | Vegesna et al. ............ 424/439 |
| 5,395,950 A | 3/1995 | Tuong |
| 5,401,858 A | 3/1995 | Huynh-Ba |
| 5,589,505 A | 12/1996 | Yu et al. |
| 5,629,298 A | 5/1997 | Dobson, Jr. |
| 5,840,896 A | 11/1998 | Van Belle et al. |
| 5,866,574 A | 2/1999 | Okamura et al. |
| 5,998,386 A | 12/1999 | Feldman |
| 5,998,387 A | 12/1999 | Belardinelli et al. |
| 6,020,321 A | 2/2000 | Cronstein et al. |
| 6,503,553 B1 | * 1/2003 | Flynn ...................... 426/564 |

FOREIGN PATENT DOCUMENTS

WO    WO 86/01508    3/1986

* cited by examiner

Primary Examiner—Raymond Henley, III
(74) Attorney, Agent, or Firm—Waddey & Patterson, PC; Douglas W. Schelling (57) ABSTRACT

This invention describes the novel use of alkyl, alkoxyl, halogenyl, or hydroxy substituted dicinnamoylquinides as therapeutic agents for enhancing adenosine levels in the brain and peripheral organs. These agents are particularly useful in treating human diseases or conditions that benefit from acute or chronic elevated levels of adenosine, such as reperfusion injury, coronary or cerebral ischemia, coronary vasoconstriction, paroxysmal supraventricular tachycardia, hypertension, wound healing, diabetes, inflammation, or sleep disturbances. They can also be used to protect normal cells from chemotoxicity in patients undergoing cancer therapy, and reverse the behavioral effects of caffeine intake.

16 Claims, 7 Drawing Sheets

3,4-di(4-chlorocinnamoyl)-1,5-quinide

Figure 3

3,4-dicaffeoyl-1,5-quinide

Figure 4

3,4-diferuloyl-1,5-quinide

Figure 5

3,4-dicoumaroyl-1,5-quinide

Figure 6

3,4-dicaffeoyl-1,5-quinide

Figure 7

Inhibition of 10 µM [³H]adenosine transport by 3,4-diferuloyl-1,5-quinide (DIFEQ) in U937 cell preparation, expressing the human adenosine *es* transporter. Nonspecific transport was defined by 1 µM NBTI.

US 6,693,128 B2

SUBSTITUTED DICINNAMOYLQUINIDES AND THEIR USE IN AUGMENTATION OF ADENONSINE FUNCTION

This application claims benefit of co-pending U.S. Provisional Patent Application Serial No. 60/290,282 filed May 11, 2001, entitled "Substituted Dicinnamoylquinides and their use in Augmentation of Adenosine Function" which is hereby incorporated by reference, and Canadian Application No. 2,347,879 filed May 16, 2001, entitled "Substituted Dicinnamoylquinides and their use in Augmentation of Adenosine Function" which is hereby incorporated by reference. Canadian Application No. 2,347,879 was received by the Canadian Intellect al Property Office, located at 50 Victoria Street, 2nd Floor Hull, Quebec K1A 0C9. The basis for priority is the Paris Convention for the Protection of Industrial Property. Another basis for priority is Canada's membership in the World Trade Organization. Be it known that we, Tomas de Paulis, a citizen of Sweden, residing at 205 Woodland Ct., Hermitage, Tenn. 37076; David M. Lovinger, a citizen of United States, residing at 2607 Sunset Place, Nashville, Tenn. 37212; and Peter Martin, a citizen of Unite States, residing at 3825 Richland Avenue, Nashville, Tenn. 37205; have invented a new and useful "Substituted Dicinnamoylquinides and their use in Augmentation of Adenosine Function."

FIELD OF THE INVENTION

The present invention relates generally to the field of use of alkyl, alkoxyl, halogenyl, or hydroxyl substituted dicinnamoylquinides. Specifically, the present invention relates to the use of the above-mentioned compounds to treat diseases or conditions that improve from either an acute or chronic increase in adenosine levels.

BACKGROUND OF THE INVENTION

Adenosine is a neuromodulator known to produce profound effects on blood flow, neurotransmission, cellular functions, and metabolism. Intracellular levels of adenosine are disclosed to be maintained by an active transport of adenosine across the cell membrane by means of a carrier-mediated, saturable nucleoside transporter, consisting of a 50 kDa protein in the form of a dimer (Thorn and Jarvis, Gen Pharmacol 27, 613–620 (1996)). This transporter protein is widely distributed in thalamic, cortical, and particularly in striatal neurons in the human brain (Glass et al, Brain Res 710, 79–91 (1996), Jennings et al, Neuropharmacol 40, 722–731 (2001)), where it regulates adenosine-dopamine interactions (Dunwiddie and Masino, Ann Rev Neurosci 24, 31–55 (2001)). Of all mammals studied, the human transporter is disclosed to be one of the most sensitive to adenosine (Hammond, N-S Arch Pharmacol 361, 373–382 (2000)), resulting in an extremely short half-life of adenosine in blood. Inhibition of the adenosine transporter is disclosed to prevent the intracellular metabolism of adenosine and prolongs the presence of high levels of adenosine (Thorn and Jarvis, Gen Pharmacol 27, 613–620 (1996). This increased level of adenosine in brain causes stimulation of adenosine receptor subtypes, similar to the effects seen from unselective adenosine receptor agonizes. Activation of the adenosine $A_{2B}$ receptor was found to increase vascular endothelial growth factor production, resulting in angiogenic neovascularization (Grant et al, Circ Res 85, 699–706 (1999). Recent studies have demonstrated that agonists for the adenosine $A_3$ receptor have antiinflammatory properties (Fishman et al, J. Cell Physiol 183, 393–398 (2000)). Both agonists at the adenosine $A_1$ and $A_3$ receptors have shown cardioprotective activity in man (Baraldi et al, Ed Res Rev 20, 103–128 (2000)), and conjugate compounds of potent adenosine $A_1$ and $A_3$ receptor agonists have shown full cardioprotection in a myocyte model of ischemia (Jacobson et al, J. Biol Chem 275, 30272–30279 (2000)).

SUMMARY OF THE INVENTION

Based on the discovery that certain naturally occurring 4-hydroxycinnamoyl di-esters of quinic acid gamma-lactone in roasted coffee (Hucke et al, Z. Lebensm Unters Forsch 180, 479–484 (1985)), but not in tea or any other caffeine containing beverages, inhibits the human adenosine transporter (de Pails et al, Eur J Pharmacol 442, 213–221 (2002)), the present invention provides, in part, methods of using 3,4-disubstituted cinnamoyl esters of quinic acid 1,5-lactone, exemplified by Formula 1, having no substituent, or a halogen atom or a hydroxyl, alkyl or alkoxyl group in either of the aromatic 3-, 4- and 5-positions to inhibit the human adenosine transporter. By inhibiting the adenosine transporter, the metabolism of intracellular adenosine is prevented resulting in increased levels of extracellular adenosine.

Figure 1:
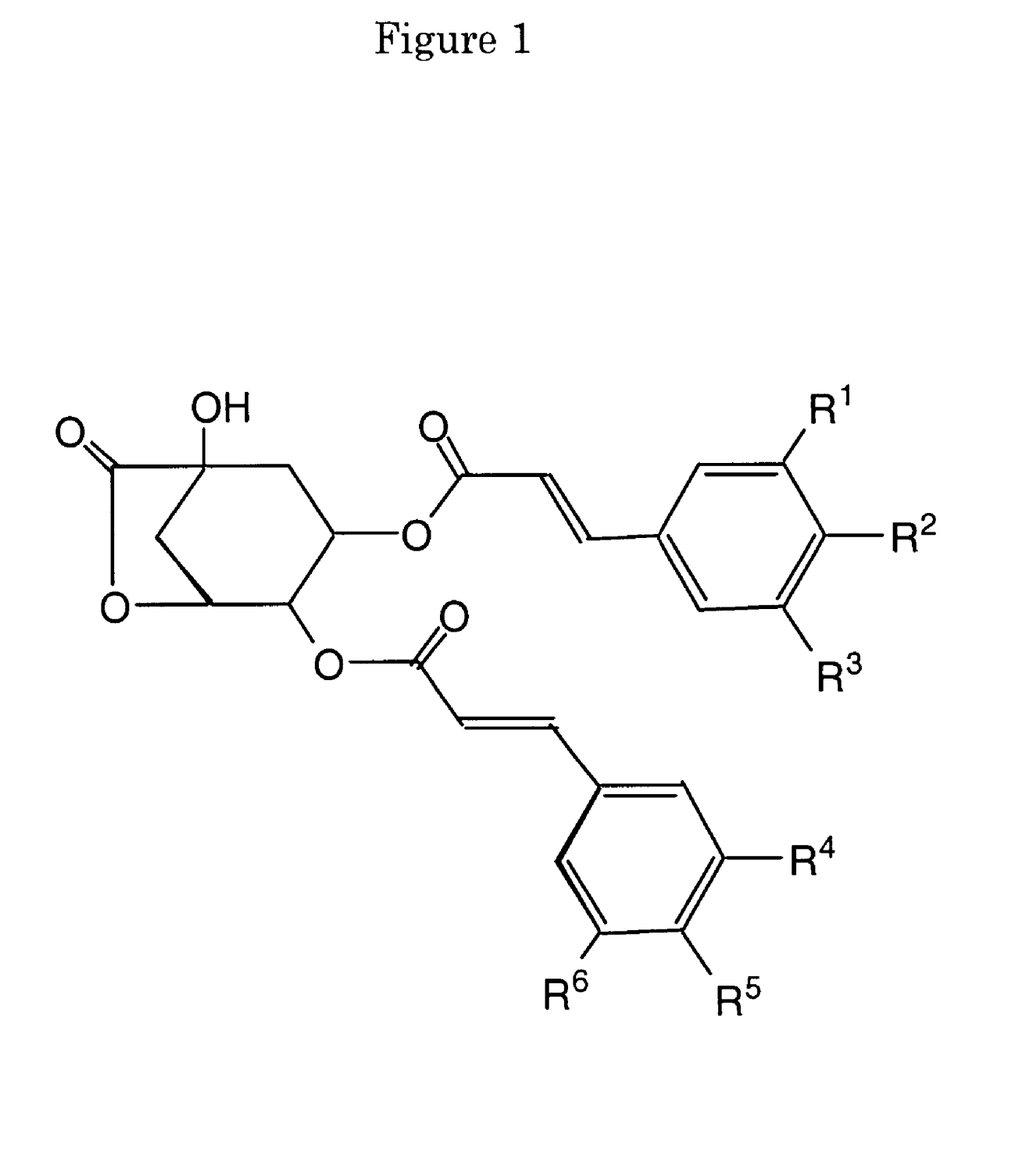
FIG. 1 is Formula 1.

Methods are provided for using compounds corresponding to Formula 1 (FIG. 1) that block the normal operation of the adenosine transporter, and preferably, result in a higher level of extra-cellular adenosine.

The present invention also provides a method of producing compounds corresponding to Formula 1.

Formula 1 is shown below:

The present invention also provides a method of delivering the compounds corresponding to Formula 1 in order to maintain a systemic level at effective concentrations.

The present invention provides fortified food products having therapeutically effective amounts of a compound having the structure of Formula 1 or a pharmaceutically acceptable salt thereof, wherein $R^1$, $R^2$, $R^3$, $R^4$, $R^5$, and $R^6$ are the same or different and each independently represents a hydrogen atom, a halogen atom, a hydroxyl group, an alkyl group, or an alkoxyl group. Such fortified food product provides the therapeutic effect of partially or completely inhibiting the adenosine transporter.

No aspect or embodiment of the present invention is bound by theory or mechanism. Various features and advantages of the invention will be apparent from the following detailed description and from the claims.

DETAILED DESCRIPTION OF THE PREFERRED EMBODIMENTS

Thus, although there have been described particular embodiments of the present invention of new and useful Substituted Dicinnamoylquinides and their use in Augmentation of Adenosine Function, it is not intended that such references be construed as limitations upon the scope of this invention except as set forth in the following claims.

3,4-disubstituted cinnamoyl esters of quinic acid 1,5-lactone, exemplified by Formula 1 (FIG. 1), having no substituent, a halogen atom or a hydroxyl, alkyl or alkoxyl group in either of the aromatic 3-, 4- and 5-positions ($R^1$–$R^6$) inhibits the human equilibrative sensitive adenosine transporter. Interruption of normal adenosine transporter function leads to increased levels of extracellular adenosine by preventing adenosine reuptake into presynaptic vesicles. The resulting elevated adenosine levels stimulate adenosine receptor subtypes, which are known to have several positive health effects, including angiogenic neovascularization, antiinflamation, and cardioprotection. Such elevated extracellular adenosine levels are additionally useful in treating human diseases or conditions that benefit from acute or chronic elevated levels of adenosine, such as reperfusion injury, coronary or cerebral ischemia, coronary vasoconstriction, paroxysmal supraventricular tachycardia, hypertension, wound healing, diabetes, inflammation, or sleep disturbances. They can also be used to protect normal cells from chemotoxicity in patients undergoing cancer therapy, and reverse the behavioral effects of caffeine intake.

The present invention is not bound by mechanism or theory.

As used herein, "Formula 1" means any chemical composition described by any text and/or figure referring to Formula 1.

As used herein, "therapeutically effective" means an amount that inhibits, completely or partially, an adenosine transporter so that the level of adenosine in the blood and/or brain increases.

As used herein, "an inappropriate extracellular adenosine level" means an extracellular adenosine level that is present when a subject has a disease or condition that improves, or a symptom of which improves, from either an acute or a chronic increase in extracellular adenosine levels. For example, but not limitation, an inappropriate extracellular adenosine level is commonly associated with cardiovascular disorders, stroke, heart attack, and depression. Other conditions that improve from an acute or a chronic increase in extracellular adenosine levels include, but are not limited to, reperfusion injury, coronary or cerebral ischemia, coronary vasoconstriction, paroxysmal supraventricular tachycardia, hypertension, wound healing, diabetes, inflammation, or sleep disturbances. Acute or chronic increases in extracellular adenosine levels also improve the symptoms of chemotoxicity in normal cells of patients undergoing cancer therapy, and reverse the behavioral effects of caffeine intake.

As used herein, "food product" means any solid or liquid that may be ingested by a subject. Commonly a food product will provide some nutritional value, although such characteristic is not necessary.

As used herein, "adenosine transporter" means human equilibrative sensitive adenosine transporter. This adenosine transporter is believed to have characteristics that are commonly found in other adenosine transporters within humans. Also, the adenosine transporter is believed to represent the characteristics of other adenosine transporters in other systems, including, but not limited to, dogs, cats, horses, cattle, and the like.

As used herein, "substituted dicinnamoylquinides" means 3,4-di-substituted (3-, 4-, or 5-mono-substituted, 3,4-, or 3,5-di-substituted, or 3,4,5-tri-substituted)-cinnamoyl-1,5-quinides.

As used herein, "pharmacologically acceptable" means molecular entities or compositions that generally do not produce adverse or allergic reactions when appropriately administered to an animal, or human.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, certain preferred methods and materials are described below. All publications, patent applications, patents, and other references mentioned herein are incorporated by reference in their entirety. Unless otherwise indicated, materials, methods, and examples described herein are illustrative only and not intended to be limiting.

Preparation of Chemical Compounds Used in Augmentation of Adenosine Function The present invention discloses a method of using certain chemical compounds to inhibit adenosine transporters. Compounds of the invention are illustrated by Formula 1, where $R^1$–$R^6$ are aromatic substituents each and independently comprised of either a hydrogen, a halogen atom, straight or branched $C_1$–$C_3$ alkyl, $C_1$–$C_3$ alkoxyl, or a hydroxyl group. The synthesis of these compounds can be accomplished by the method of Wynne et al. (WO 8601508, 1986) as described by Huynh-Ba (U.S. Pat. No. 5,401,858), Tuong (U.S. Pat. No. 5,395,950, 1995), which are hereby incorporated by reference. Briefly, it consists of condensing an excess of the appropriately protected substituted cinnamoyl acid chloride with 1-(2,2,2-trichloroethoxycarbonyl)-1,5-quinide, prepared by lactonization of quinic acid in acetone with p-toluenesulfonic acid, followed by condensation of the remaining free hydroxyl group with 2,2,2-trichloroethyl chloroformate to give 1-O-(2,2,2-trichloroethoxycarbonyl)-3,4-O-isopropylidene- 1,5-quinide and hydrolysis of the isopropylidene group in 90% aqueous trichloroacetic acid. Removal of the 2,2,2-trichloroethoxyformyl group and other phenolic protection groups, if present, gives the final product, which can be purified by fractional crystallization from organic solvents, such as ethyl acetate, chloroform, or isopropylether.

In certain embodiments, the Formula 1 compounds will be administered in a pharmaceutical composition in therapeutically effective amounts. Those of ordinary skill in the art will readily be able to prepare Formula 1 compounds, as described herein, and to inhibit the adenosine transporter based upon the data detailed herein. It is contemplated that many routes of administration may be utilized in conjunction with the Formula 1 compounds of the invention, such as intravenous injection or oral consumption, which are described in greater detail below.

Inhibition of An Adenosine Transporter

Figure 2:
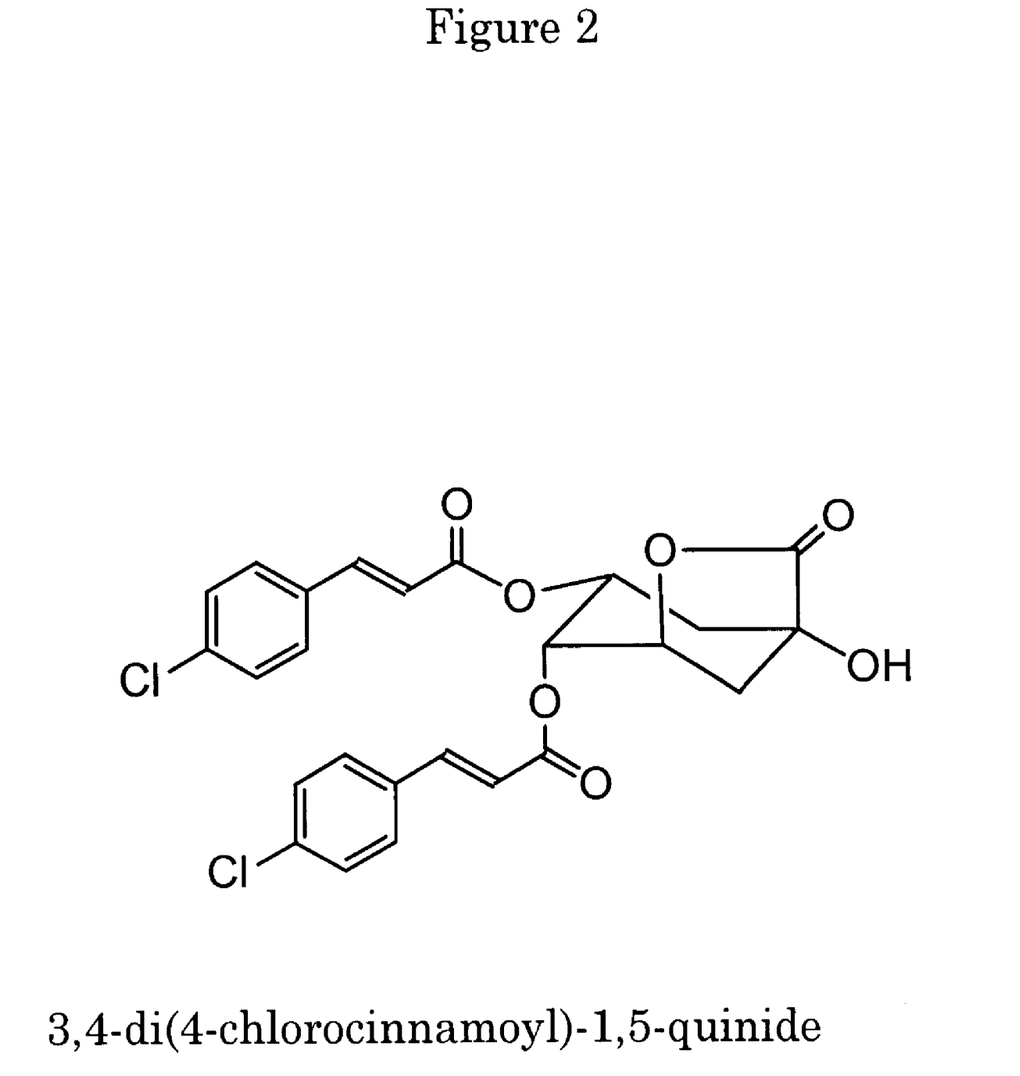
FIG. 2 is the structure of 3,4-di(4-chlorocinnamoyl)-1,5-quinide.
Figure 3:
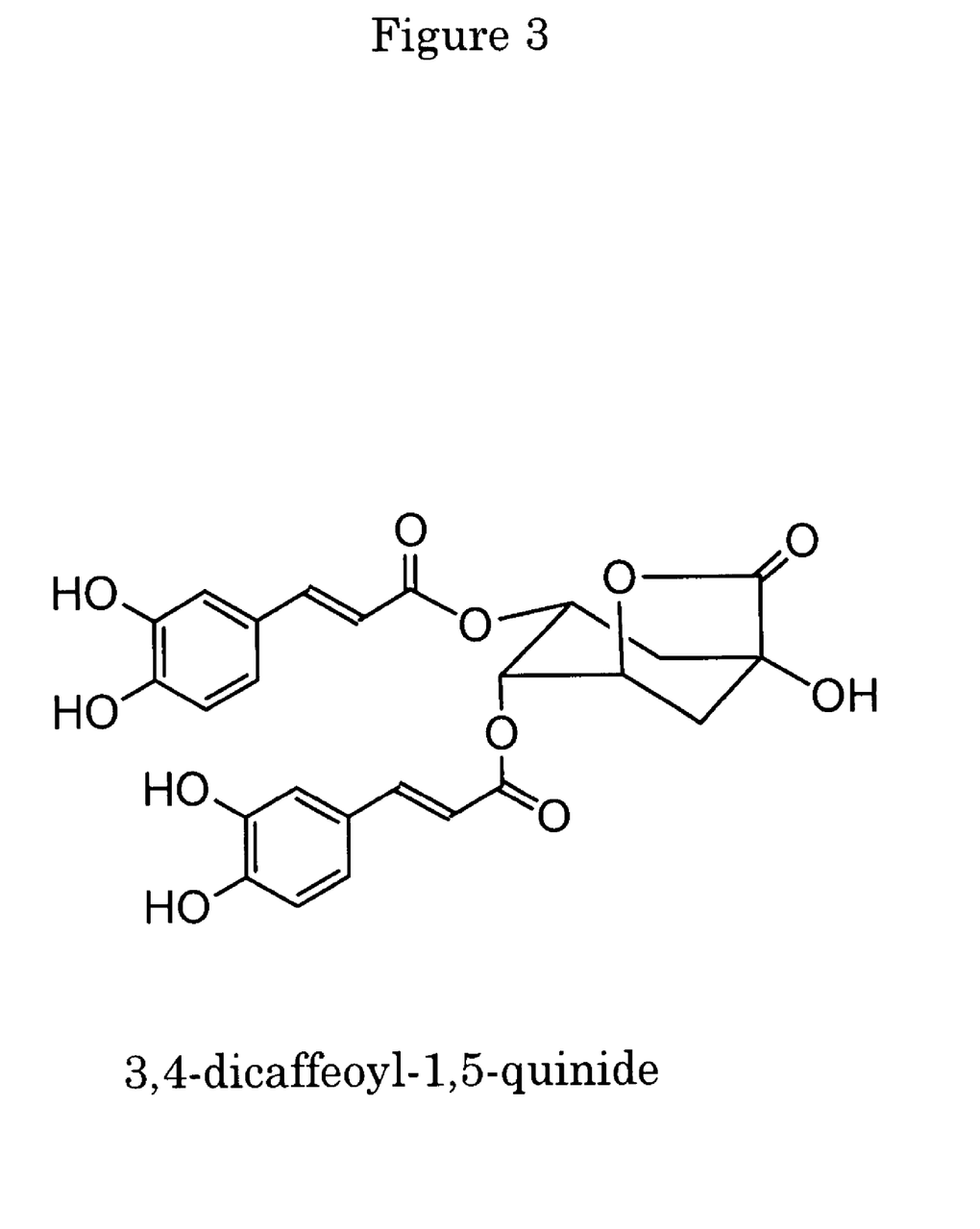
FIG. 3 is the structure of 3,4-dicaffeoyl-1,5-quinide.
Figure 4:
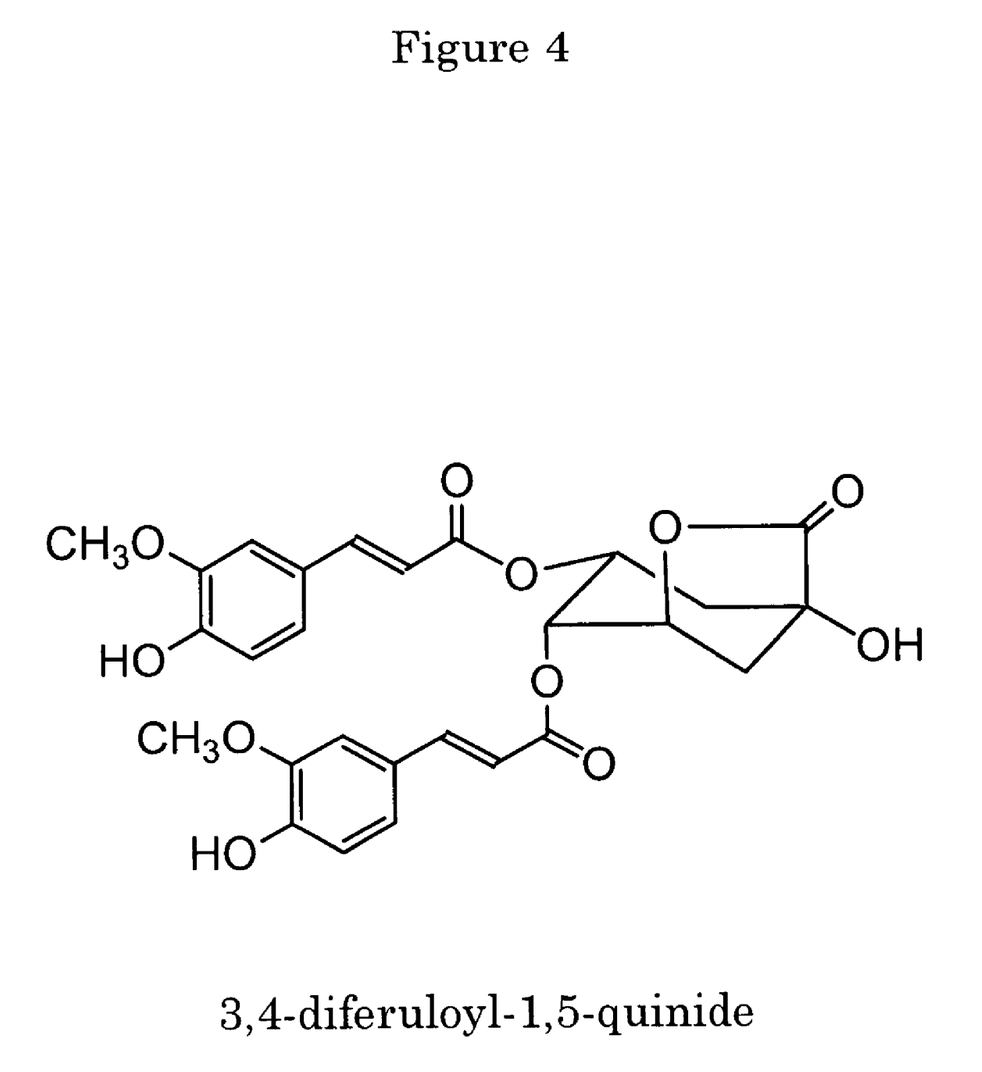
FIG. 4 is the structure of 3,4-diferuloyl-1,5-quinide.
Figure 5:
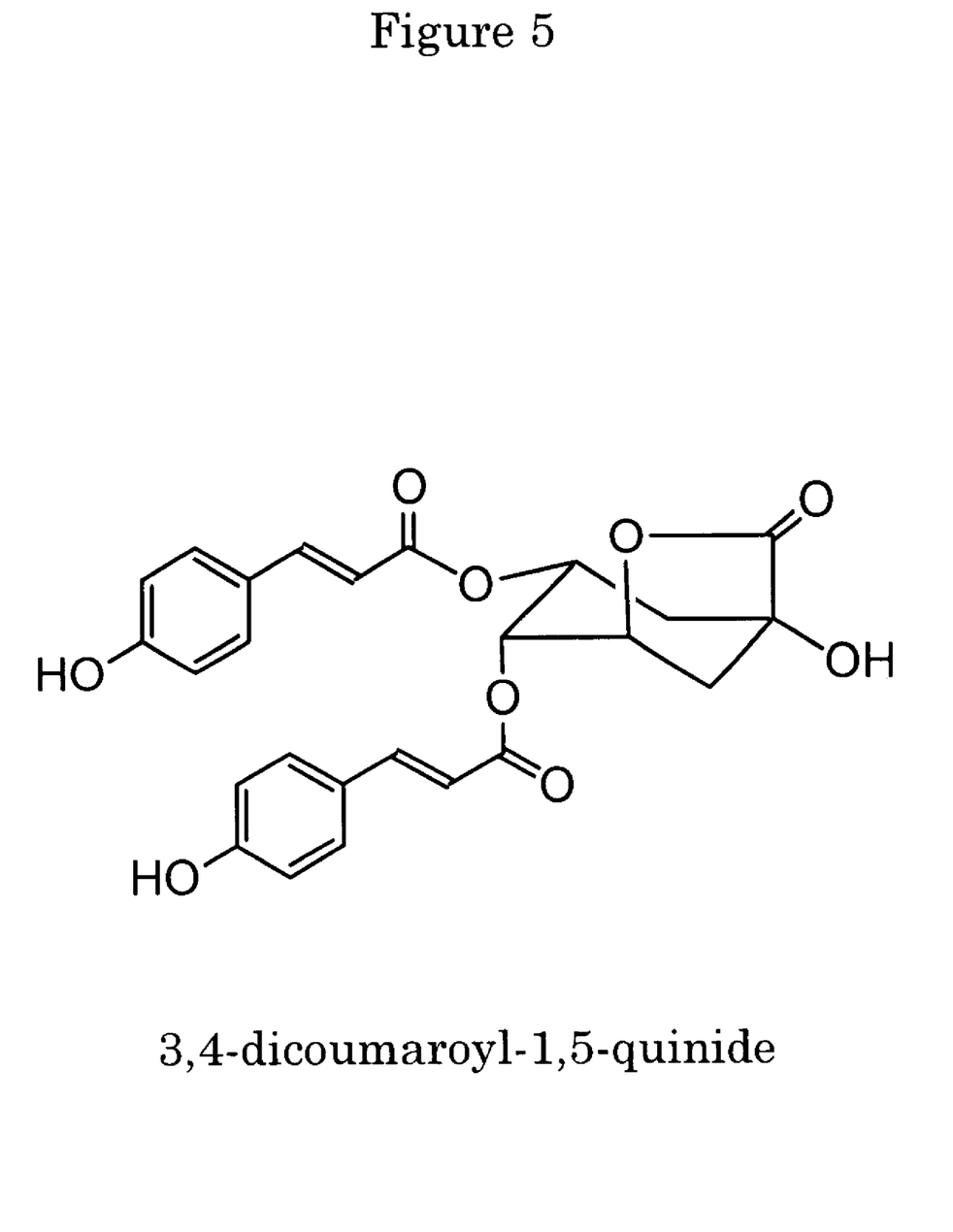
FIG. 5 is the structure of 3,4-dicoumaroyl-1,5-quinide.

The ability of the compounds of this invention to inhibit the adenosine transporter is evaluated in several different experiments. First, as further described in Example 6, the inhibition of [$^3$H]adenosine transport by 3,4-diferuloyl-1,5-quinide, shown in FIG. 4, was measured by a technique commonly known in the art which is further described within Example 6. Based upon the structural features of the other compositions disclosed herein, it is reasonable to believe that such other compositions also have the ability to inhibit adenosine transport. More specifically, Example 6 discloses prophetic examples in which 3,4-di(4-chlorocinnamoyl)-1,5-quinide (shown in FIG. 2), 3,4-dicaffeoyl-1,5-quinide (shown in FIG. 3), and 3,4-dicoumaroyl-1,5-quinide (shown in FIG. 5) are used to inhibit [$^3$H]adenosine transport. The above-mentioned compositions are reasonably believed to provide such inhibition. Additionally, the remainder of the compositions disclosed herein are also reasonably believed to provide the inhibition of adenosine transport. In certain embodiments, the inhibition described in this paragraph is partial. In other embodiments, the inhibition described in this paragraph is complete.

A second experimental system was also used to establish the function of the compositions disclosed herein. As further described in Example 7, several of the compositions disclosed herein were capable of displacing [3H]NBTI ((S)-(4-nitrobenzyl)-6-thioinosine) binding in U-937 cell homogenates expressing the human adenosine transporter. The experiments demonstrating the inhibition of adenosine transport and the additional experiments demonstrating the ability of the compositions to displace [3H]NBTI binding are clear evidence that the compositions can be used in methods of treating inappropriate extracellular adenosine levels in a subject in need thereof Since it has been experimentally proven that at least one of the compounds described herein inhibit the human adenosine transporter in the experimental system described, it is predictable and reasonable to believe that such inhibition occurs with other adenosine transporters in other systems. Accordingly, the invention should not be limited to human adenosine transporters, but should include adenosine transporters in dogs, cats, horses, cattle, domestic birds, and the like.

Amount of the Chemical Compound to be Administered in Augmentation of Adenosine Function The quantity to be administered of a composition disclosed herein depends on several factors. The most important factor is the mass of subject being treated. Formula 1 compounds will be administered in a manner compatible with the dosage formulation and in such amount as is therapeutically effective. In certain embodiments, the present invention of providing a method of treating an inappropriate extracellular adenosine level in a subject in need thereof will comprise administering to the subject a therapeutically effective amount of a compound of Formula 1 or a pharmaceutically acceptable formulation thereof. In certain embodiments, the therapeutically effective amount of the Formula 1 compound is less than 9 milligrams per kilogram of body weight of the subject. In other embodiments, the therapeutically effective amount of the Formula 1 compound is more than 10 milligrams per kilogram of body weight of the subject. In other certain embodiments, the therapeutically effective amount of the Formula 1 compound is from about 10 milligrams per kilogram of body weight of the subject to about 30 milligrams per kilogram of body weight of the subject. In still other embodiments, the therapeutically effective amount of the Formula 1 compound is from about 30 milligrams per kilogram of body weight of the subject to about 80 milligrams per kilogram of body weight of the subject. In a preferred embodiment, the Formula 1 compound is administered as 20 milligrams per kilogram of body weight of the subject.

In certain embodiments, the therapeutically effective amount of a Formula 1 compound is from about 10 milligrams per kilogram of body weight of the subject to about 80 milligrams per kilogram of body weight of the subject. More specifically, in certain embodiments in which 3,4-dicaffeoyl-1,5-quinide (estimated to comprise 35 mg per average cup of coffee) is being administered, the therapeutically effective amount is from about 3 milligrams per kilogram of body weight of the subject to about 80 milligrams per kilogram of body weight of the subject.

Frequency of Administration of the Chemical Compounds Used in Augmentation of Adenosine Function As described above, the therapeutically effective amount of a Formula 1 compound either partially or completely inhibits the adenosine transporter, which results in an increased extracellular adenosine level in the blood and/or brain. Accordingly, a therapeutically effective amount of a Formula 1 compound should be administered at a frequency so that the adenosine transporter remains either partially or completely inhibited. In certain embodiments, a therapeutically effective amount of a Formula 1 compound is administered more than once per 24 hour period. In other embodiments, a therapeutically effective amount of a Formula 1 compound is administered less than once per 24 hour period. In still other embodiments, a therapeutically effective amount of a Formula 1 compound is administered at least 3 times per 24 hour period. In certain embodiments, a therapeutically effective amount of a Formula 1 compound is administered from about 1 to about 10 times per 24 hour period. In certain embodiments, a therapeutically effective amount of a Formula 1 compound is administered 1, 2, 3, 4, 5, 6, 7, 8, 9, or 10 times per 24 hour period. The formulations are easily administered in a variety of dosage forms, such as the type of injectable solutions described below.

Manner of Administering the Chemical Compounds Used in Augmentation of Adenosine Function The present invention also provides a method of treating an inappropriate extracellular adenosine level in a subject in need thereof, comprising administering to the subject a therapeutically effective amount of a compound of Formula 1 or a pharmaceutically acceptable salt thereof, wherein $R_1$–$R_6$ are the same or different and each independently represent substituents selected from the group consisting of a hydrogen atom, a halogen atom, a hydroxyl group, an alkyl group, and an alkoxyl group; wherein the adenosine transporter is partially or completely inhibited by the treatment.

In certain embodiments, the inappropriate extracellular adenosine level is associated with cardiovascular disorders, stroke, heart attack, or depression. In other embodiments, the present invention also provides a method of treating a subject in need thereof, comprising administering to the subject a therapeutically effective amount of a compound of Formula 1 or a pharmaceutically acceptable salt thereof, wherein $R_1$–$R_6$ are the same or different and each independently represent substituents selected from the group consisting of a hydrogen atom, a halogen atom, a hydroxyl group, an alkyl group, and an alkoxyl group; wherein the adenosine transporter is partially or completely inhibited by the treatment.

The present invention further provides methods to inhibit the adenosine transporter, the method comprising administering to said adenosine transporter a composition comprising Formula 1, wherein said administration results in an inhibition of the adenosine transporter. In particular embodiments, the adenosine transporter is the human equilibrative sensitive adenosine transporter. Particularly preferred compounds of the present invention are compounds of Formula 1 where both cinnamoyl groups are comprised of aromatic 4-chloro, 4-hydroxy, or 4-methoxy substituents, or where the aromatic substituents are 3,4-dichloro atoms or 3,4-dihydroxy or 3,4-dimethoxy groups.

The compounds represented by Formula 1 are introduced using any suitable method. A "suitable method" of introduction is one that places a Formula 1 compound in a position to inhibit, either partially or completely, the adenosine transporter. In certain embodiments, the administering step of a method of treating an inappropriate extracellular adenosine level in a subject in need thereof is via oral, topical, subcutaneous, intramuscular, intravenous or patenteral routes. In some preferred embodiments, the administering step comprises administering the compound more than once. For example, injection, oral, and inhalation methods may be employed, with one of ordinary skill in the art being able to determine an appropriate method of introduction for a given circumstance. Preferably, the composition used to inhibit the adenosine transporter, either partially or completely, is administered by oral solution.

In some preferred embodiments, injection will be used. This injection may be intravenous, intraperitoneal, intramuscular, subcutaneous, intratumoral, intrapleural, or of any other appropriate form. The form of the injectable compositions is typically a liquid or suspension. Additionally, these preparations also may be emulsified. Intravenous vehicles include fluid and nutrient replenishers. Other pharmaceutically acceptable carriers include aqueous solutions, non-toxic excipients, including salts, preservatives, buffers and the like.

In certain embodiments, a beverage or food serves as the excipient. For example, fortified beverages and food products include, but are not limited to: aqueous carriers, water, coffee, tea, alcoholic/aqueous solutions, saline solutions, parenteral vehicles such as sodium chloride, Ringer's dextrose, etc. Preservatives include antimicrobial agents, anti-oxidants, chelating agents and inert gases. Accordingly, in certain embodiments, a fluid type food product is fortified with one compound disclosed herein, or more than one compound disclosed herein. In other embodiments, a solid type food product is fortified with one compound disclosed herein, or more than one compound disclosed herein.

Methods for this use of Formula 1 compounds are described herein. In certain embodiments, substituted dicinnamoylquinides are ingested as food additives. In other embodiments, the present invention provides a compound of Formula 1 fortified food product, comprising a food product and a therapeutically effective amount of a compound of Formula 1, to provide partial inhibition of an adenosine transporter. In still other embodiments, the above-mentioned Formula 1 fortified food product will provide complete inhibition of the adenosine transporter. For example, coffee and other drinks and foods may be fortified with compounds corresponding to Formula 1.

In certain embodiments of the invention, Formula 1, and related, compounds are ingested in conjunction with the consumption of coffee or more preferred coffee fortified therewith. Oral formulations, in addition to containing the Formula 1 compounds, may include other components, such as pharmaceutical grades of mannitol, lactose, starch, magnesium stearate, sodium saccharine, cellulose, magnesium carbonate, and the like. The compositions may take the form of solutions, suspensions, tablets, pills, gels, capsules, sustained release formulations or powders. When the route is topical, the form may include a cream, ointment, salve, spray, or other carrier.

One aspect of the present invention is the use of Formula 1 compounds in pharmaceutical compositions. The pH and exact concentration of the various components in the pharmaceutical are adjusted according to well known parameters typically related to storage or comfort during injection.

In certain embodiments, the present invention provides a method for treating a human suffering from an inappropriate extracellular adenosine level, or suffering from a condition that is improved by an acute or chronic increase in adenosine level, which comprises administration of a therapeutically effective amount of a compound of Formula I, wherein $R^1$–$R^6$ are the same or different and each independently represents a hydrogen atom, a halogen atom, a hydroxyl group, an alkyl group, or an alkoxyl group; wherein the adenosine transporter is partially or completely inhibited by the treatment. The above-mentioned method is also a method for the treatment of depression associated within appropriate adenosine levels. In other embodiments, the present invention provides a method for the treatment of cardiovascular disorders associated with inappropriate adenosine levels. In still other embodiments, the present invention provides a method for the treatment of a heart attack associated with inappropriate adenosine levels. In still further embodiments, the method for treating a human suffering from an inappropriate extracellular adenosine level, is also a method for the treatment of stroke associated with inappropriate adenosine levels.

In certain embodiments, a disease condition is not diagnosed or is deemed unrelated to adenosine levels; however the subject is still in need of treatment to increase said levels. The need for increasing adenosine levels is generally determined by a physician or attending healthcare professional (including a veterinarian).

In certain other aspects of the present invention there are provided therapeutic kits comprising a suitable container and a pharmaceutical formulation of a Formula 1 compound. Such a kit may further comprise a pharmaceutical formulation of a Formula 1 compound.

In some embodiments of the present invention, the discovery that Formula 1 compounds are able to inhibit the adenosine transporter will be used in combination with other therapies that also increase adenosine function, such as adenosine receptor agonists. There may be other technologies that are used in combination with the present invention in order to increase the extracellular adenosine level of a subject. These other therapies are distinguishable from the present invention due to their interaction with the adenosine receptors, rather than the adenosine transporter. These other therapies may be known at the time of this application, or may become apparent after the date of this application.

All references described in this patent application, including the previously filed U.S. Provisional Patent Application Serial No. 60/290,282, and Canadian Application No. 2,347,879 are hereby incorporated herein by reference, in their entirety. The present invention is further illustrated by the following specific examples. The examples are provided for illustration only and are not to be construed as limiting the scope or content of the invention in any way.

EXAMPLE 1

Preparation of 3,4-Di(4-Chlorocinnamoyl)-1,5-Guinide

Five grams (27 mmol) of 4-chlorocinnamic acid (Aldrich) is dissolved in 50 mL toluene, followed by 5 mL (68 mmol) of thionyl chloride and 0.3 mL dimethylformamide as catalyst. The mixture is heated to 60° C. for 2 h. The solvent is evaporated and the residue is used direct in the next step. 4-Chorocinnamoyl chloride is dissolved in 25 mL of $CH_2Cl_2$ and added dropwise to a mixture of 3.5 g (10 mmol) of 1-O-(2,2,2-trichloroethoxycarbonyl)-1,5-quinide and 2 g (25 mmol) of pyridine in 50 mL of $CH_2Cl_2$ at 0° C. (ice-EtOH). After 16 h at 20° C. the solvent is removed and the residue is extracted with 2×200 mL ethyl acetate. Washing with 2×50 mL of 1 N HCl to remove the pyridine, then with 2×50 mL of 2% $NaHCO_3$ to remove excess acid, followed by 100 mL of water, drying ($Na_2SO_4$), evaporation of the solvent, and crystallization from 100 mL of ethyl acetate gave 5.3 g of 3,4-di(4-chlorocinnamoyl)-1-O-(2,2,2-trichloroethoxy-carbonyl)-1,5-quinide. Yield 79%. $^1$H-NMR: δ ppm 7.68 (d, J=16 Hz, 9'-CH=), 7.60, (d, J=16 Hz, 9''-CH=), 7.47 (d, J=9 Hz, 2H, 2',6'-Ar), 7.40 (d, J=9 Hz, 2H, 3',5'-Ar), 7.38 (d, J=9 Hz, 2H, 2'',6''-Ar), 7.31 (d, J=9 Hz, 2H, 3'',5''-Ar), 6.51 (d, J=16 Hz, 8'-CH=), 6.30, (d, J=16 Hz, 8''-CH=), 5.72 (t, 4-$CH_{eq}$), 5.36 (ddd, 3-$CH_{ax}$), 5.04 (t, 5-$CH_{eq}$), 4.86 (d, J=12 Hz, 1-OCOOCHCCl$_3$), 4.75 (d, J=12 Hz, 1-OCOOCHCCl$_3$), 3.23 (m, 6-$CH_{ax}$), 2.72 (d, 6-$CH_{eq}$), 2.58 (m, 2-$CH_{eq}$), 2.47 (t, 2-$CH_{ax}$).

The protected quinide is dissolved in 100 mL of THF, addition of 1 g (15 mmol) of zinc powder (65 mesh) and 50 mL acetic acid at 20° C. Stirring for 3 h, evaporation of the solvents, extraction with 2×200 mL ethyl acetate, washing with 50 mL 1 N NaOH, then 50 mL water, drying ($Na_2SO_4$) and evaporation of the solvent gave 3,4-di(4-chlorocinnamoyl)-1,5-quinide. Recrystallization from chloroform gave 2.9 g of pure product. Mp 172° C. Yield 78%. $^1$H-NMR: δ ppm 7.68 (d, J=16 Hz, 9'-CH=), 7.60, (d, J=16 Hz, 9''-CH=), 7.47 (d, J=9 Hz, 2H, 2',6'-Ar), 7.40 (d, J=9 Hz, 2H, 3',5'-Ar), 7.38 (d, J=9 Hz, 2H, 2'',6''-Ar), 7.31 (d, J=9 Hz, 2H, 3'',5''-Ar), 6.48 (d, J=16 Hz, 8'-CH=), 6.30, (d, J=16 Hz, 8''-CH=), 5.08 (t, 4-$CH_{eq}$), 5.31 (ddd, 3-$CH_{ax}$), 4.95 (q, 5-$CH_{eq}$), 3.09 (b, 1-OH), 2.58 (d, 6-$CH_{ax}$), 2.50 (m, 6-$CH_{eq}$), 2.37 (m, 2-$CH_{eq}$), 2.21 (t, 2-$CH_{ax}$).

EXAMPLE 2

Preparation of 3,4-Diferuloyl-1,5-Guinide

Six grams (16 mmol) of 4-O-(2,2,2-trichloroethoxycarbonyl)feruloyl chloride is dissolved in 25 mL of $CH_2Cl_2$ and added dropwise to a mixture of 2 g (5.7 mmol) of 1-O-(2,2,2-trichloroethoxycarboxyl)-1,5-quinide and 2 g (25 mmol) of pyridine in 25 mL of $CH_2Cl_2$ at 0° C. (ice-EtOH). After 16 h at 20° C. the solvent is removed and the residue is extracted with 300 mL ethyl acetate. Washing with 50 mL of 1 N HCl to remove the pyridine, then with 50 mL of 2% $NaHCO_3$ to remove excess acid, followed by 50 mL of water, drying ($Na_2SO_4$), evaporation of the solvent, and crystallization from 100 mL of ethyl acetate gave 5 g of 3,4-di[4-O-(2,2,2-trichloroethoxycarboxyl)feruloyl]-1-O-(2,2,2-trichloroethoxycarbonyl)-1,5-quinide. (Yield 83%). Mp 232–234° C. $^1$H-NMR: δ ppm 7.69 (d, J=16 Hz, 9'-CH=), 7.61, (d, J=16 Hz, 9''-CH=), 7.20 (m, 6'-CH+6''-CH), 7.12 (m, 2'-CH+2''-CH), 7.00 (m, 5'-CH+5''-CH), 6.47 (d, 8'-CH=), 6.30, (d, 8''-CH=), 5.74 (t, 4-$CH_{eq}$), 5.38 (m, 5-$CH_{eq}$), 5.03 (t, 3-$CH_{ax}$), 4.88 (s, 4'-$CH_2OCOO$), 4.86 (s, 4''-$CH_2OCOO$), 4.79 (dd, 1-$CH_2OCOO$), 3.87 (s, 3'-$OCH_3$), 3.78 (s, 3''-$OCH_3$), 3.21 (d, 6-$CH_{ax}$), 2.75 (m, 6-$CH_{eq}$), 2.56 (m, 2-$CH_{eq}$), 2.52 (t, 2-$CH_{ax}$).

Deprotection of all trichloroethoxycarbonyl groups is accomplished by dissolving 5 g (4.7 mmol) of 3,4-di[4-O-(2,2,2-trichloroethoxycarbonyl)feruloyl]-1-O-(2,2,2-trichloroethoxycarbonyl)-1,5-quinide in 50 mL of THF, addition of 1 g (15 mmol) of zink powder (65 mesh) and 50 mL acetic acid at 20° C. Stirring for 3 h, evaporation of the solvents, extraction with 2×75 mL ethyl acetate, washing with 2×25 mL 2% $NaHCO_3$, then 50 mL water, drying ($Na_2SO_4$) and evaporation of the solvent gives a non-crystalline residue. It is dissolved in 15 mL of ethyl acetate and 15 mL of isopropyl ether is added. Filtration gave 2.1 g (85%) of 3,4-diferuloyl-1,5-quinide. Mp 142–144° C. Rotation [α]$^{20}$D+196 deg (c 0.88, DMSO). $^1$H-NMR: δ ppm 7.67 (d, J=15.9 Hz, 9'-CH=), 7.55, (d, J=15.8 Hz, 9''-CH=), 7.11 (dd, 6'-CH), 7.09 (dd, 6''-CH), 7.01 (m, 2'-CH+2''-CH), 6.95 (d, 5'-CH), 6.83 (d, 5''-CH), 6.36 (d, J=15.9 Hz, 8'-CH=), 6.19, (d, J=15.8 Hz, 8''-CH=), 5.69 (t, 4-$CH_{eq}$), 5.29 (m, 3-$CH_{ax}$), 4.95 (t, 5-$CH_{eq}$), 3.93 (s, 3'-$OCH_3$), 3.81 (s, 3''-$OCH_3$), 2.65 (d, 6-$CH_{ax}$), 2.54 (m, 6-$CH_{eq}$), 2.41 (m, 2-$CH_{eq}$), 2.32 (t, 2-$CH_{ax}$).

$^{13}$C-NMR: δ ppm 177 (7-C=O), 166 (7'-C=O), 165 (7''-C=O), 149 (4'-COH), 148 (4''-COH), 147 (3'-COCH$_3$), 147 (3''-COCH$_3$), 147 (9'-CH=), 146 (9''-CH=), 129 (1'-C), 129 (1''-C), 126 (6'-CH), 125 (6''-CH), 123 (8'-CH=), 123 (8''-CH=), 115 (5'-CH), 115 (5''-CH), 114 (2'-CH), 114 (2''-CH), 74 (4-CH), 72 (5-CH), 68 (1-OH), 66 (3-CH), 38 (6-$CH_2$), 37 (2-$CH_2$).

EXAMPLE 3

Preparation of 3,4-Dicoumaroyl-1,5-Guinide 3,4-dicoumaroyl-1,5-quinide is prepared as described in example 2, starting with 4-hydroxycinnamic acid. Mp 233–235° C. Rotation [α]$^{20}$D+145 deg (c 0.25, DMSO). $^1$H-NMR: δ ppm 7.68 (d, J=16 Hz, 9'-CH=), 7.56 (d, J=16 Hz, 9''-CH=), 7.49 (d, 2H, J=8 Hz, 2',6'-CH), 7.35 (d, 2H, J=8 Hz, 2'',6''-CH), 6.85 (d, 2H, J=8 Hz, 3',5'-CH), 6.87 (d, 2H, J=8 Hz, 3'',5''-CH), 6.36 (d, J=16 Hz, 8'-CH=), 6.19 (d, J=16 Hz, 8''-CH=), 5.67 (t, 4-$CH_{eq}$), 5.29 (m, 3-$CH_{ax}$), 4.95 (t, 5-$CH_{eq}$), 2.61 (d, 6-$CH_{ax}$), 2.54 (m, 6-$CH_{eq}$), 2.43 (m, 2-$CH_{eq}$), 2.23 (t, 2-$CH_{ax}$).

EXAMPLE 4

Preparation of 3,4-Dicaffeoyl-1,5-Guinide

Figure 6:
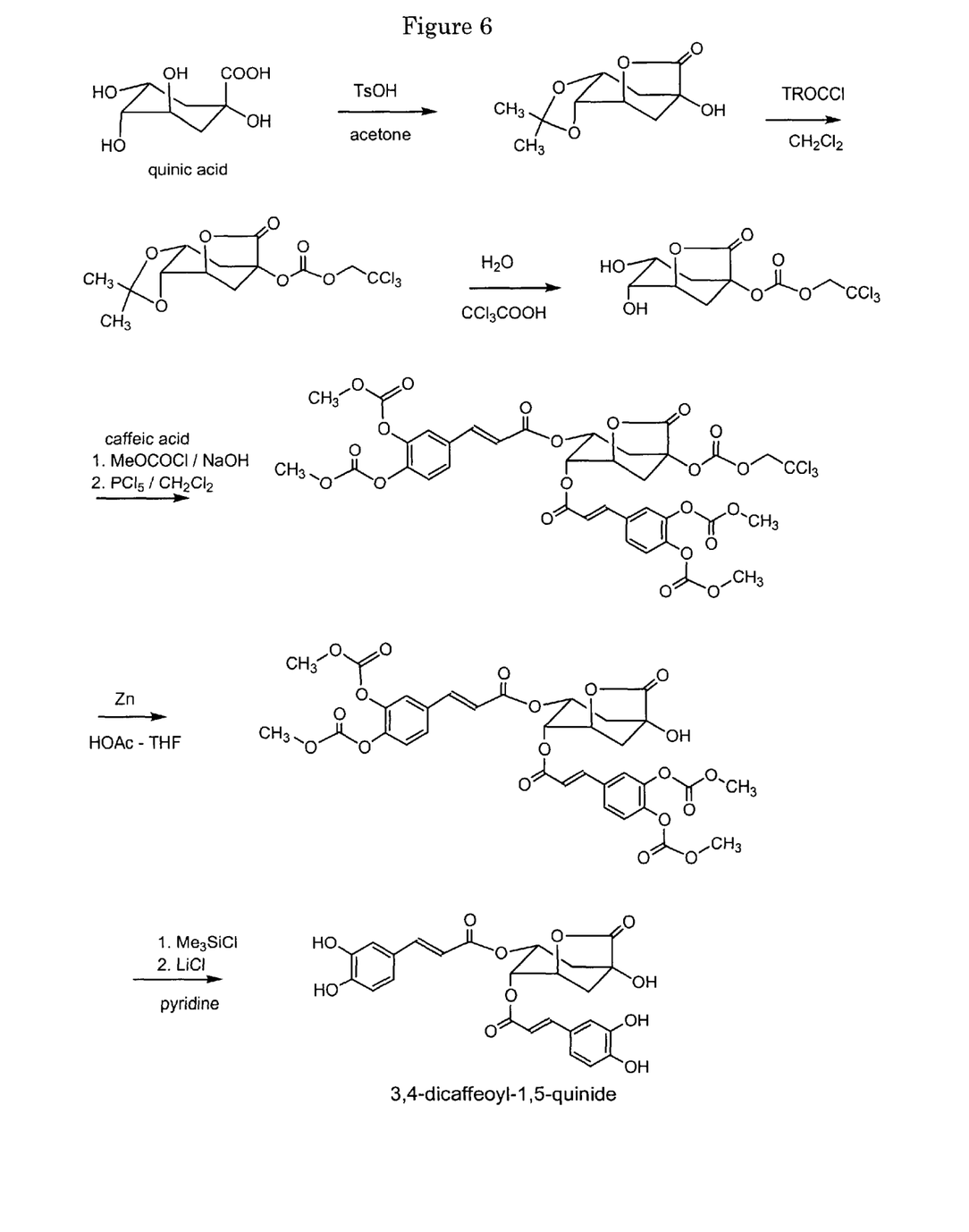
FIG. 6 is a flow chart for the synthesis of 3,4-dicaffeoyl-1,5-quinide.

A flow chart of the preparation of 3,4-dicaffeoyl-1,5-quinide is shown in FIG. 6.

3,4-Dicaffeoyl-1,5-quinide is prepared as described in example 2, except that the starting material is 3,4- dihydroxycinnamic acid and the phenolic protecting groups are methoxyformyl groups and the deprotection reagent is lithium chloride in refluxing pyridine. $^1$H-NMR (CDCl$_3$-DMSO-d$_6$): δ ppm 7.62 (d, J=15 Hz, 9'-CH═), 7.40, (d, J=15 Hz, 9"-CH═), 7.10 (s, 2'-CH), 7.06 (m, 6'-CH), 6.99 (s, 2"-CH), 6.85 (m, 6"-CH), 6.77 (d, 5'-CH), 6.68 (d, 5"-CH), 6.36 (d, J=15 Hz, 8'-CH═), 6.12, (d, J=15 Hz, 8"-CH═), 5.47 (t, 4-CH$_{eq}$), 5.02 (t, 3-CH$_{ax}$), 4.93 (m, 5-CH$_{eq}$), 2.49 (d, 6-CH$_{ax}$), 2.35 (m, 6-CH$_{eq}$), 2.19 (m, 2-CH$_{eq}$), 2.03 (t, 2-CH$_{ax}$).

EXAMPLE 5

Preparation of Intermediates
3,4-Isopropylidene-1,5-Guinide.

A suspension of 15 g (78 mmol) of quinic acid (Aldrich) and 0.5 g of p-toluenesulfonic acid in 300 mL of acetone are heated to refluxing temperature for 20 h with the solvent passing through a Soxhlet extractor supplied with 15 g of molecular sieve (4 A), that previously have been activated under vacuum for 2 h at 140° C. The clear solution is cooled to 5° C., 4 g (48 mmol) of NaHCO$_3$ is added, and the mixture is stirred for 1 h. Filtration and evaporation of the solvent, followed by crystallization by dissolving the residue in 150 mL of CH$_2$Cl$_2$ and addition of 150 mL hexane gave 16 g of 3,4-isopropylidene-1,5-quinide (yield 96%). Mp 140–142° C. $^1$H-NMR: δ ppm 4.72 (m, 5-CH$_{eq}$), 4.50 (m, 4-CH$_{eq}$), 4.31 (m, 3-CH$_{ax}$), 2.90 (b, 1-COH), 2.78 (d, 6-CH$_{ax}$), 2.34 (m, 6-CH$_{eq}$+2-CH$_{eq}$), 2.17 (dd, 2-CH$_{ax}$), 1.52 (s, CCH$_3$), 1.33 (s, CCH$_3$).

1-O-(2,2,2-Trichloroethoxycarbonyl)-3,4-O-isopropylidene-1,5-guinide.

Sixteen g (75 mmol) of 3,4-isopropylidene-1,5-quinide (Aldrich) is dissolved in 150 mL of CH$_2$Cl$_2$ and 14 mL (173 mmol) of anhydrous pyridine is added, followed by drop-wise addition of a solution of 17 g (81 mmol) 2,2,2-trichloroethyl chloroformate (Aldrich) in 25 mL of CH$_2$Cl$_2$ at 0° C. After stirring at room temperature for 2 h, 200 mL of CH$_2$Cl$_2$ is added and the mixture is washed with 2×75 mL 1 N HCl, then with 50 mL water. Drying with anhydrous Na$_2$SO$_4$, evaporation of the solvent to 100 mL, then adding 400 mL of EtOH gave 20 g of 1-O-(2,2,2-trichloroethoxycarbonyl)-3,4-O-isopropylidene-1,5-quinide (yield 68%). Mp 164–166° C. $^1$H-NMR: δ ppm 4.84 (t, 5-CH$_{eq}$), 4.80 (dd, OCH$_2$CCl$_3$), 4.56 (dd, 4-CH$_{eq}$), 4.34 (d, 3-CH$_{ax}$), 3.06 (d, 6-CH$_{ax}$), 2.66 (m, 6-CH$_{eq}$), 2.57 dd, 2-CH$_{eq}$), 2.40 (dd, 2-CH$_{ax}$), 1.53 (s, CCH$_3$), 1.34 (s, CCH$_3$).

1-O-(2,2,2-Trichloroethoxycarbonyl)-1,5-guinide.

Three mL of water is added to 27 g (165 mmol) of trichloroacetic acid and stirred with warming until clear solution, then 20 g (51 mmol) of 1-O-(2,2,2-trichloroethoxycarbonyl)-3,4-O-isopropylidene-1,5-quinide is added in portions at 20° C. Stirring for 4 h, then 200 mL of ice-water and 400 mL of ethyl acetate are added, followed by slowly addition of a solution of 15 g (178 mmol) of NaHCO$_3$ in 400 mL water. The organic layer is separated and washed with 50 mL of 2% NaHCO$_3$, then with 50 mL water. Drying and evaporation of the solvent, addition of 150 mL of 70° C. toluene, cooling over night, and filtration of the crystals gives 12 g (67%) of 1-O-(2,2,2-trichloroethoxycarbonyl)-1,5-quinide. Mp 130–131° C. $^1$H-NMR: δ ppm 4.93 (t, 5-CH$_{eq}$), 4.77 (dd, OCH$_2$CCl$_3$), 4.18 (t, 4-CH$_{eq}$), 4.02 (t, 3-CH$_{ax}$), 3.04 (d, 6-CH$_{ax}$), 2.68 (m, 6-CH$_{eq}$), 2.36 (m, 2-CH$_{eq}$), 2.17 (t, 2-CH$_{ax}$).

4-O-(2,2,2- Trichloroethoxycarbonyl)ferulic Acid.

Ten g (51 mmol) of 3-methoxy-4-hydroxycinnamic acid (Aldrich) is dissolved in 140 mL of 1 N NaOH followed by drop-wise addition of 13 g (61 mmol) of 2,2,2-trichloroethyl chloroformate at 0° C. After 20 min the mixture is neutralized with 2 N HCl and the precipitation is collected by filtration. Recrystallization from 300 mL 50% of aqueous EtOH gave 16 g of 4-O-(2,2,2-trichloroethylcarbonyl)-3-methoxycinnamic acid (yield 85%). Mp 192° C. $^1$H-NMR: δ ppm 7.75 (d, J=15.9 Hz, 3'-CH═), 7.18 (m, 3H, ArH), 6.42 (d, J=15.8 Hz, 2'-CH═), 4.89 (s, OCH$_2$CCl$_3$), 3.90 (s, OCH$_3$).

4-O-(2,2,2-Trichloroethoxycarboxyl)feruloyl Chloride.

Seven g (19 mmol) of 4-0-(2,2,2-trichloroethylcarbonyl)-3-methoxy-cinnamic acid (Aldrich) is dissolved in 75 mL of CH$_2$Cl$_2$, 5 g (24 mmol) of PCl$_5$ was added at 20° C., and the mixture is heated to 35° C. for 20 min. Evaporation of the solvent under vacuum and addition of 200 mL of hexane gave 6 g of 4-O-(2,2,2-trichloroethoxy-carbonyl)feruloyl chloride (yield 81%). Mp 186° C. $^1$H-NMR: δ ppm 7.79 (d, J=15.5 Hz, 3'-CH═), 7.18 (m, 3H, ArH), 6.61 (d, J=15.5 Hz, 2'-CH═), 4.89 (s, OCH$_2$CCl$_3$), 3.91 (s, OCH$_3$).

EXAMPLE 6

Evaluation of Adenosine Transport Inhibition

Inhibition of [$^3$H]adenosine transport in homogenates of U-937 cell culture (American Tissue Culture Compository), expressing the human (es) transporter is performed according to Gu et al, J. Neurochem 67, 972–977 (1996), which is incorporated herein by reference. Rate of transport is determined in HEPES buffer at 37° C. for 30 min (with choline replacing sodium). Full displacement curves for the adenosine transporter are obtained by using 8 concentrations of each compound, increasing by a factor of 2 and ranging from 0.25 μM-32 μM. Nonspecific transport is defined with 1 μM NBTI ((S)-(4-nitrobenzyl)-6-thioinosine). Cell cultures are grown in high glucose Dulbecco's modified Eagle's medium supplemented with NaHCO$_3$ (40 mM), 10% fetal bovine serum (Gibco), 400 mg/L geneticin, and 0.1 mM hypoxanthine.

Briefly, the cells are cultured at 37° C. under a CO$_2$/air (5/95, v/v) in tissue culture flasks (75 cm$^2$, Falcon). When reaching confluency (70–80%), cells are trypsinized and harvested by centrifugation. Harvested cells are re-suspended in 50 mM TRIS buffer at 4° C. (0.1 mg/mL), the cell membranes are disrupted by Polytron homogenization (12,500 rpm for 25 s), and the suspension is centrifuged at 30,000×g for 60 min. The supernatant is discarded and remaining the pellet is resuspended in 50 mM TRIS buffer to 0.2 mg–0.5 mg protein/mL and frozen at −80° C. until used.

For further details regarding some of the above-mentioned commonly known protocols, see generally, Sambrook et al., 2001, Molecular Cloning: A Laboratory Manual (3rd Edition), Cold Spring Harbor Press, Cold Spring Harbor, N.Y.

Figure 7:
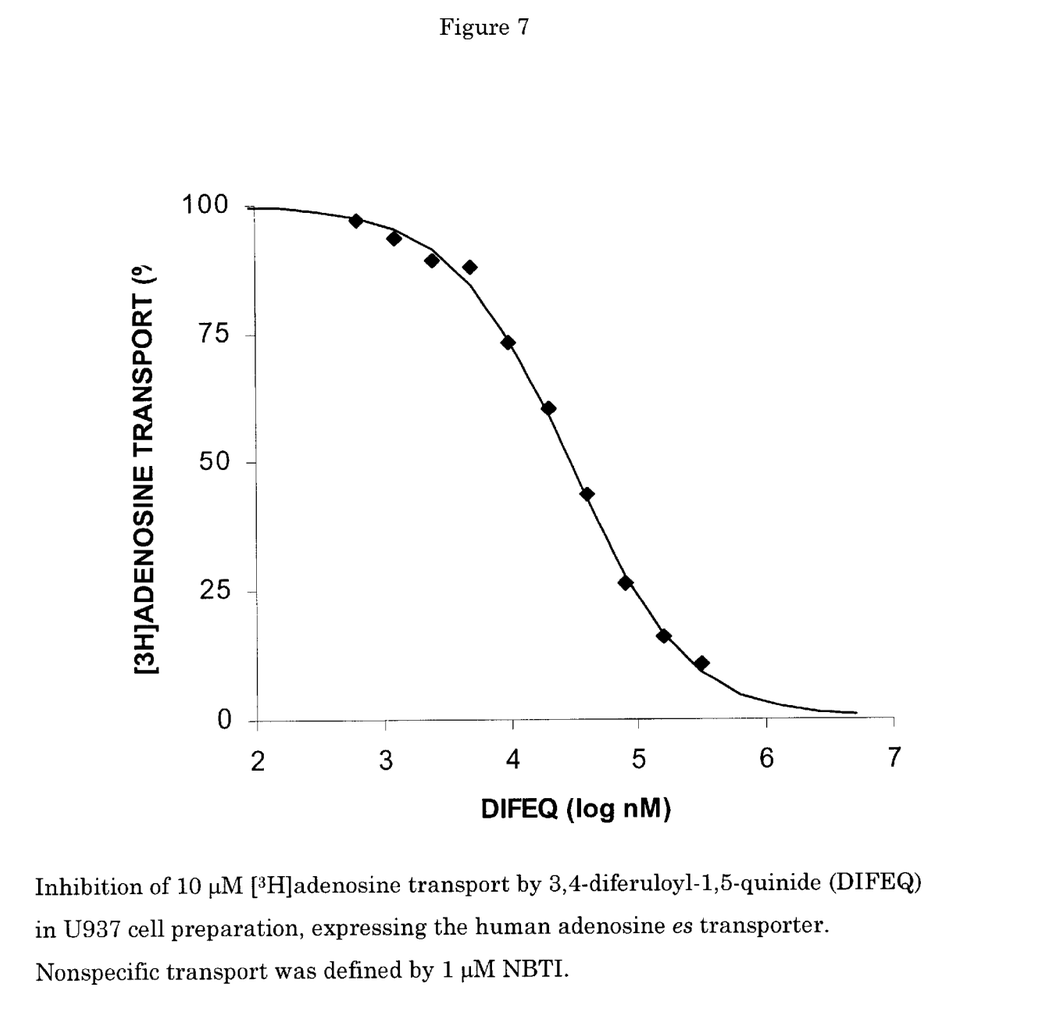
FIG. 7 is a chart showing inhibition of adenosine transport by 3,4-diferuloyl-1,5-quinide.

3,4-diferuloyl-1,5-quinide was able to inhibit the transport of adenosine. The transport of 10 μM [$^3$H]adenosine was blocked by a typical agent of this invention, described in example 2, with an inhibitory constant $K_i$ of 1.2 μM. The inhibition is shown in FIG. 7.

Further testing of other compounds, as discussed above, will produce similar, if not identical, results. More specifically, when 3,4-di(4-chlorocinnamoyl)-1,5-quinide, 3,4-dicaffeoyl-1,5-quinide, and 3,4-dicoumaroyl-1,5-quinide are independently prepared in 8 concentrations, increasing by a factor of 2 and ranging from 0.25–32 μM, in order to obtain a full displacement curve for the adenosine transporter, it is believed that such displacement curves would be similar to the results shown in FIG. 7.

EXAMPLE 7

Evaluation of Adenosine Transporter Binding Affinity

Evaluation of the inhibition of [$^3$H]NBTI ((S)-(4-nitrobenzyl)-6-thioinosine) binding in homogenates of U-937 cell culture, expressing the human es transporter is performed according to Marangos et al, J. Neurochem 39, 184–191 (1982), incorporated herein by reference. The cell membranes in final concentration of 0.03 mg protein/mL are incubated with [$^3$H]NBTI at 2–4 nM concentration in 50 mM TRIS buffer (pH 7.5) at 4° C. for 1.5 h in a total volume of 1.0 mL. Nonspecific binding is defined with 10 μM NBTI. Each determination is carried out in triplicate. Bound and free [$^3$H]NBTI are separated by vacuum filtration through fiberglass filters (Schleicher & Schuell, Keene, N.H.) that are presoaked with 0.3% polyethylenimine for 10 min, using a Brandel M-24R cell harvester. The filters are washed three times for 10 s with ice-cold 50 mM TRIS buffer and placed in 10 mL scintillation fluid (Cytoscint, ICN).

Beta spectrometry is performed using a Beckman L5801 instrument at 47% counting efficiency. IC$_{50}$ values and Hill slopes (n$_H$) are calculated from log-logit analysis of competition binding data. K$_i$ values of the competing ligand are calculated from IC$_{50}$ values using the Cheng-Prusoff equation, $$K_i = IC_{50}/(1+L/K_D)$$

where L is the concentration of the [3H]NBTI and K$_D$=0.32 nM is the equilibrium dissociation constant obtained from Scatchard analysis of the binding. Data are expressed as mean±standard error of the mean (SEM).

Displacement of [3H]NBTI binding in U-937 cell homogenates, expressing the human adenosine transporter by substituted dicinnamoyl-1,5-quinides of Formula 1.

g 2,3-dihydroxybutanedioic acid, 10 g 1,2,3-propanetriol, and 500 g sucrose. After cooling to room temperature the mixture is flavored and colored with suitable additives, such as sugar and food coloring, to produce 50 doses of a beverage containing 400 mg active ingredient per 200 mL.

What is claimed is:

1. A method of treating an inappropriate extr cellular adenosine level in a subject in need thereof, comprising: administerin to the subject a therapeutically effective amount of a compound having the formula or a pharmaceutically acceptable salt thereof wherein R$^1$, R$^2$, R$^3$, R$^4$, R$^5$, and R$^6$ are the same or different and each independently represents a substituent selected from the group consisting of a hydrogen atom, a halogen atom, a hydroxyl group, an alkyl group, and an alkoxyl group.

2. The method of claim 1, wherein the inappropriate extracellular adenosine level is in cardiovascular disorders.

3. The method of claim 1, wherein the inappropriate extracellular adenosine level is associated with a stroke.

4. The method of claim 1, wherein the inappropriate extracellular adenosine level is in a heart attack.

5. The method of claim 1, wherein the inappropriate extracellular adenosine level is in depression.

6. The method of claim 1, wherein administering to the subject the therapeutically effective amount of the com-

|  | Substituents | | | | |
|---|---|---|---|---|---|
| Active ingredient | R1 | R2 | R3 | Affinity (Ki μM) | Hill slope |
| 3,4-di(4-chlorocinnamoyl)-1,5-quinide | H | Cl | H | 1.3 ± 0.0 | 1.12 ± 0.00 |
| 3,4-dicaffeoyl-1,5-quinide | OH | OH | H | 2.4 ± 0.7 | 1.00 ± 0.03 |
| 3,4-diferuloyl-1,5-quinide | OCH$_3$ | OH | H | 0.96 ± 0.13 | 0.94 ± 0.02 |
| 3,4-dicoumaroyl-1,5-quinide | H | OH | H | 0.96 ± 0.07 | 1.22 ± 0.11 |

Substituents (R$^4$–R$^6$) of the second cinnamoyl group are identical to those of the first. A Hill slope close to unity indicates binding to a single site.

EXAMPLE 8

Preparation of Pharmaceutical Formulations

Capsules.

800 g of the active ingredient (compound corresponding to Formula 1), 1 g magnesium stearate, 5 g sodium laurylsulfate, 50 g lactose, 50 g starch, and 1 g colloidal silicon dioxide are mixed thoroughly and the mixture is filled into 1000 gelatin capsules each containing 800 mg of the active ingredient (compound corresponding to Formula 1).

Oral Solution.

20 g of the active ingredient (compound corresponding to Formula 1) is dissolved by stirring in 10 L warm water kept at 50–70° C., containing 5 g methyl 4-hydroxybenzoate, 10 pound further comprises administering through a route selected from the group consisting of oral, inhalation, topical, subcutaneous, intramuscular, intravenous, and parenteral.

7. The method of claim 1, wherein the therapeutically effective amount is sufficient to raise adenosine levels in blood and brain.

8. The method of claim 1, wherein administering to the subject the therapeutically effective amount of the compound further comprises administering the compound more than once.

9. The method of claim 1, wherein an adenosine transporter is partially or completely inhibited by the treatment.

10. The method of claim 9, wherein the adenosine transporter is a human equilibrative sensitive adenosine transporter.

11. The method of claim 1, wherein the compound is selected from the group consisting of 3,4-di(4-chlorocinnamoyl)-1,5-quinide, 3,4-dicaffeoyl-1,5-quinide, 3,4-diferuloyl-1,5-quinide, and 3,4-dicoumaroyl-1,5-quinide.

12. A method for treating a human suffering from an inappropriate extra-cellular adenosine level, which comprises administration of a therapeutically effective amount of a compound having the formula or a pharmaceutically acceptable salt thereof, wherein $R^1$, $R^2$, $R^3$, $R^4$, $R^5$, and $R^6$ are the same or different and each independently represents a hydrogen atom, a halogen atom, a hydroxyl group, an alkyl group, or an alkoxyl group; wherein the adenosine transporter is partially or completely inhibited by the treatment.

13. The method of claim 12, wherein the method is for the treatment of depression associated with inappropriate adenosine levels.

14. The method of claim 12, wherein the method is for the treatment of cardiovascular disorders associated with inappropriate adenosine levels.

15. The method of claim 12, wherein the method is for the treatment of heart attack associated with inappropriate adenosine levels.

16. The method of claim 12, wherein the method is for the treatment of stroke associated with inappropriate adenosine levels.

* * * * *